(12) United States Patent
Cryer

(10) Patent No.: US 6,280,465 B1
(45) Date of Patent: Aug. 28, 2001

(54) APPARATUS AND METHOD FOR DELIVERING A SELF-EXPANDING STENT ON A GUIDE WIRE

(75) Inventor: Brett W. Cryer, Sunnyvale, CA (US)

(73) Assignee: Advanced Cardiovascular Systems, Inc., Santa Clara, CA (US)

(*) Notice: Subject to any disclaimer, the term of this patent is extended or adjusted under 35 U.S.C. 154(b) by 0 days.

(21) Appl. No.: 09/475,601

(22) Filed: Dec. 30, 1999

(51) Int. Cl.$^7$ ............................................. A61F 2/06
(52) U.S. Cl. ............................................. 623/1.11
(58) Field of Search ............................. 606/108, 198, 606/200, 190, 194; 623/1.23, 1.18, 1, 1.2, 1.11

(56) References Cited

U.S. PATENT DOCUMENTS

| | | |
|---|---|---|
| 4,300,244 | 11/1981 | Bokros . |
| 4,512,338 | 4/1985 | Balko et al. . |
| 4,538,622 | 9/1985 | Samson et al. ...................... 604/170 |
| 4,554,929 | 11/1985 | Samson et al. ...................... 604/95 |
| 4,580,568 | 4/1986 | Gianturco ............................. 604/96 |
| 4,655,771 | 4/1987 | Wallsten ............................... 606/1 |
| 4,740,207 | 4/1988 | Kreamer ............................... 606/1 |
| 4,762,128 | 8/1988 | Rosenbluth ........................... 604/96 |
| 4,795,458 | 1/1989 | Regan ................................... 623/1 |
| 4,830,003 | 5/1989 | Wolff et al. ........................... 623/1 |
| 4,878,906 | 11/1989 | Lindemann et al. ................. 623/1 |
| 4,886,062 | 12/1989 | Wiktor ................................... 623/1 |
| 4,893,623 | 1/1990 | Rosenbluth .......................... 606/192 |
| 4,907,336 | 3/1990 | Gianturco ............................. 29/515 |
| 4,913,141 | 4/1990 | Hillstead ............................... 606/108 |
| 4,950,227 | 8/1990 | Savin et al. .......................... 604/8 |
| 4,969,458 | 11/1990 | Wiktor ................................... 606/194 |
| 4,969,890 | 11/1990 | Sugita et al. ........................ 606/192 |
| 4,990,155 | 2/1991 | Wilkoff ................................. 606/191 |
| 4,994,071 | 2/1991 | MacGregor ......................... 606/194 |
| 4,998,539 | 3/1991 | Delsanti ............................... 128/898 |
| 5,002,560 | 3/1991 | Machold et al. ..................... 606/198 |
| 5,026,377 | 6/1991 | Burton et al. ........................ 606/108 |
| 5,034,001 | 7/1991 | Garrison et al. ..................... 604/53 |
| 5,035,706 | 7/1991 | Giantureo et al. .................. 606/198 |
| 5,037,392 | 8/1991 | Hillstead .............................. 604/96 |
| 5,037,427 | 8/1991 | Harada et al. ....................... 606/108 |
| 5,041,126 | 8/1991 | Gianturco ............................ 606/195 |
| 5,059,166 | 10/1991 | Fischell et al. ..................... 600/3 |

(List continued on next page.)

FOREIGN PATENT DOCUMENTS

| | | |
|---|---|---|
| 2102019 | 6/1997 | (CA) . |
| 0 423 916 A1 | 4/1991 | (EP) . |
| 0 556 940 A1 | 8/1993 | (EP) . |
| 0 626 153 A1 | 11/1994 | (EP) . |
| 0 852 933 A2 | 7/1997 | (EP) . |
| WO 95/33422 | 12/1995 | (WO) . |
| WO 96/39998 | 12/1996 | (WO) . |
| WO 96/41592 | 12/1996 | (WO) . |
| WO 98/49983 | 11/1998 | (WO) . |
| WO 99/49809 | 10/1999 | (WO) . |
| WO 00/71058 | 11/2000 | (WO) . |

OTHER PUBLICATIONS

Wallace, et al., Tracheobronchial Tree; Expandable Metallic Stents Used in Experimental and Clinical Applications, *Radiology*, pp. 309–312, Feb. 1986.

Primary Examiner—Cary E. O'Connor
(74) Attorney, Agent, or Firm—Fulwider Patton Lee & Utecht, LLP

(57) ABSTRACT

An assembly for delivering a self-expanding stent to an intraluminal location comprising a guide wire, a retainer to secure the stent to the guide wire in a compressed configuration, and a release member to release the stent from the retainer and allow the stent to assume an expanded configuration. The stent may be compressed by axial elongation, radial compression, or linear elongation into a generally tube-like configuration. The release member may operate the retainer to release the stent or urge the stent away from contact with the retainer.

17 Claims, 2 Drawing Sheets

U.S. PATENT DOCUMENTS

| | | | |
|---|---|---|---|
| 5,061,275 | 10/1991 | Wallsten et al. | 606/1 |
| 5,064,435 | 11/1991 | Porter | 623/12 |
| 5,071,407 | 12/1991 | Termin et al. | 604/104 |
| 5,078,720 | 1/1992 | Burton et al. | 606/108 |
| 5,089,005 | 2/1992 | Harada | 606/194 |
| 5,089,006 | 2/1992 | Stiles | 606/198 |
| 5,092,877 | 3/1992 | Pinchuk | 600/1 |
| 5,108,416 | 4/1992 | Ryan et al. | 606/194 |
| 5,123,917 | 6/1992 | Lee | 606/1 |
| 5,135,517 | 8/1992 | McCoy | 604/281 |
| 5,158,548 | 10/1992 | Lau et al. | 604/96 |
| 5,163,952 | 11/1992 | Froix | 606/1 |
| 5,163,958 | 11/1992 | Pinchuk | 606/11 |
| 5,171,262 | 12/1992 | MacGregor | 606/1 |
| 5,183,085 | 2/1993 | Timmermans | 623/1 |
| 5,192,297 | 3/1993 | Hull | 606/195 |
| 5,197,978 | 3/1993 | Hess | 623/1 |
| 5,222,969 | 6/1993 | Gillis | 606/194 |
| 5,222,971 | 6/1993 | Willard et al. | 606/158 |
| 5,226,913 | 7/1993 | Pinchuk | 623/1 |
| 5,242,451 | 9/1993 | Harada et al. | 606/108 |
| 5,256,146 | 10/1993 | Ensminger et al. | 604/104 |
| 5,258,020 | 11/1993 | Froix | 613/1 |
| 5,263,964 | 11/1993 | Purdy | 606/200 |
| 5,282,823 | 2/1994 | Schwartz et al. | 606/198 |
| 5,282,824 | 2/1994 | Gianturco | 606/198 |
| 5,304,200 | 4/1994 | Spaulding | 606/198 |
| 5,306,294 | 4/1994 | Winston et al. | 623/1 |
| 5,345,937 | 9/1994 | Middleman et al. | 604/95 |
| 5,354,308 | 10/1994 | Simon et al. | 606/198 |
| 5,354,309 | 10/1994 | Schnepp-Pesch et al. | 606/198 |
| 5,372,600 | 12/1994 | Beyer et al. | 606/108 |
| 5,378,239 | 1/1995 | Termin et al. | 604/104 |
| 5,395,390 | 3/1995 | Simon et al. | 606/198 |
| 5,403,341 | 4/1995 | Solar | 606/198 |
| 5,405,377 | 4/1995 | Cragg | 623/1 |
| 5,405,380 | 4/1995 | Gianotti et al. | 623/1 |
| 5,411,507 | 5/1995 | Heckle | 606/108 |
| 5,415,664 | 5/1995 | Pinchuk | 606/108 |
| 5,443,496 | 8/1995 | Schwartz et al. | 606/195 |
| 5,453,090 | 9/1995 | Martinez et al. | 604/53 |
| 5,456,667 | 10/1995 | Ham et al. | 604/107 |
| 5,456,794 | 10/1995 | Marin et al. | 606/198 |
| 5,458,615 * | 10/1995 | Klemm et al. | 606/198 |
| 5,478,349 | 12/1995 | Nicholas | 606/198 |
| 5,484,444 | 1/1996 | Braunschweiler et al. | 606/108 |
| 5,496,277 | 3/1996 | Termin et al. | 604/104 |
| 5,514,154 | 5/1996 | Lau et al. | 606/195 |
| 5,522,883 | 6/1996 | Slater et al. | 623/1 |
| 5,534,007 * | 7/1996 | St. Germain et al. | 606/108 |
| 5,554,181 | 9/1996 | Das | 623/1 |
| 5,569,295 | 10/1996 | Lam | 606/198 |
| 5,571,135 * | 11/1996 | Fraser et al. | 623/1 |
| 5,591,197 | 1/1997 | Orth et al. | |
| 5,603,721 | 2/1997 | Lau et al. | 606/195 |
| 5,634,928 | 6/1997 | Fischell et al. | 606/108 |
| 5,637,089 | 6/1997 | Abrams et al. | |
| 5,643,339 | 7/1997 | Kavteladze et al. | |
| 5,653,759 | 8/1997 | Hogan et al. | |
| 5,690,643 | 11/1997 | Wijay | |
| 5,690,644 | 11/1997 | Yurek et al. | 606/108 |
| 5,707,376 | 1/1998 | Kavteladze et al. | 606/108 |
| 5,709,703 | 1/1998 | Lukic et al. | 606/198 |
| 5,725,570 | 3/1998 | Heath | 606/195 |
| 5,776,142 | 7/1998 | Gunderson | |
| 5,800,526 | 9/1998 | Anderson et al. | 623/1 |
| 5,824,041 | 10/1998 | Lenker et al. | |
| 5,843,119 | 12/1998 | Shmulewitz | 606/198 |
| 5,935,135 | 8/1998 | Bramfitt et al. | 606/108 |
| 6,042,588 * | 3/2000 | Munsinger et al. | 606/108 |
| 6,051,021 | 4/2000 | Frid | 606/195 |
| 6,059,810 | 5/2000 | Brown et al. | 606/198 |
| 6,086,610 | 7/2000 | Duerig et al. | 623/1 |

* cited by examiner

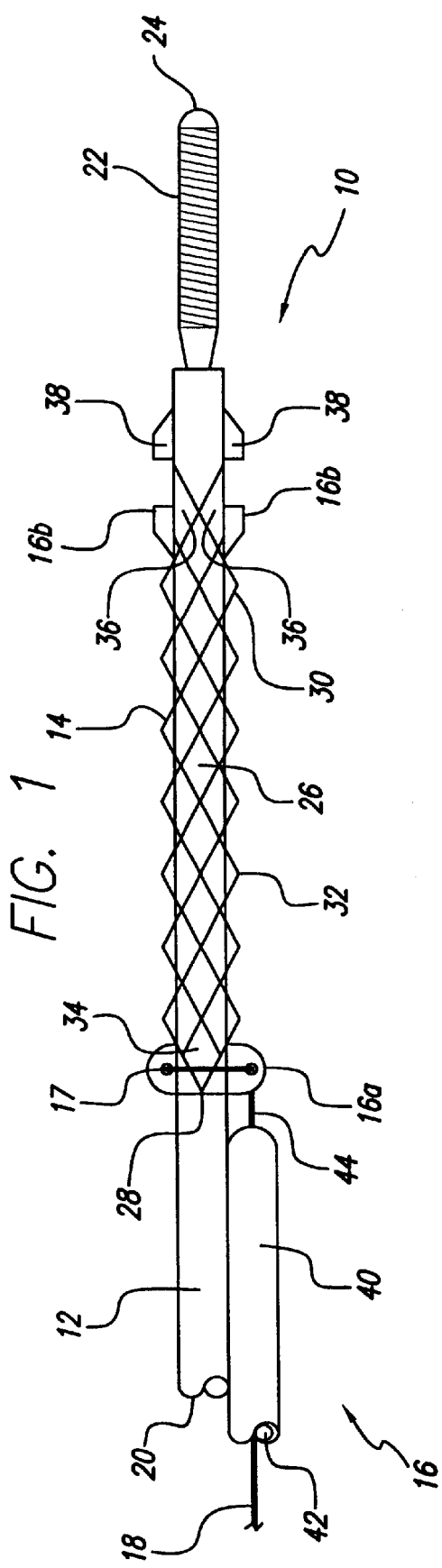
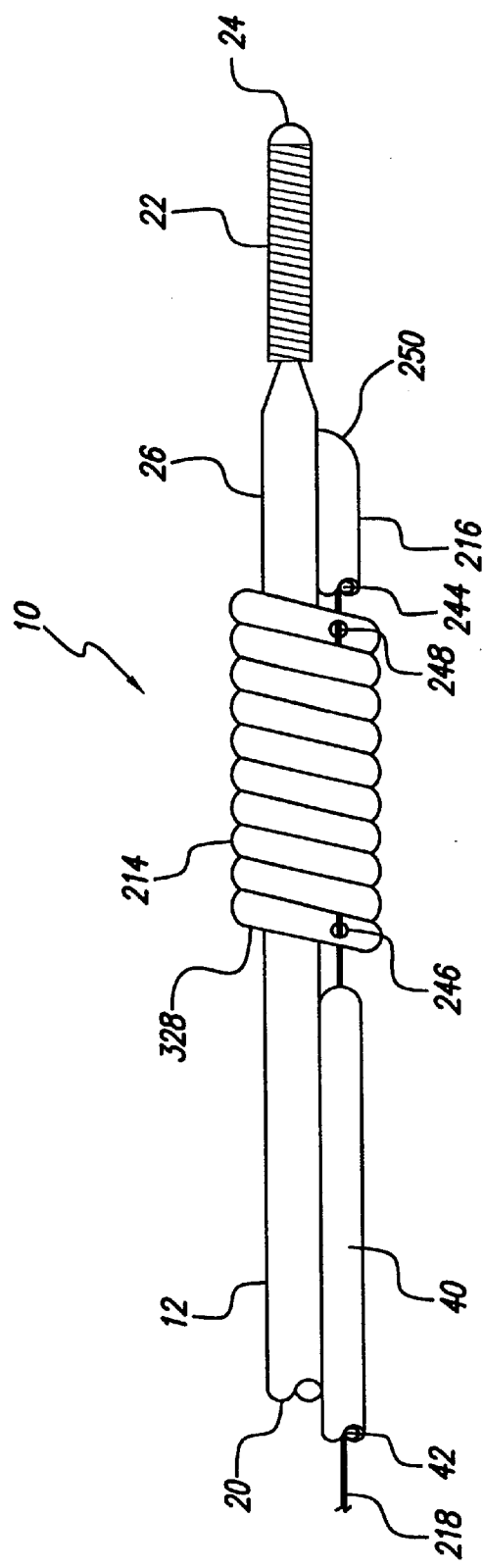

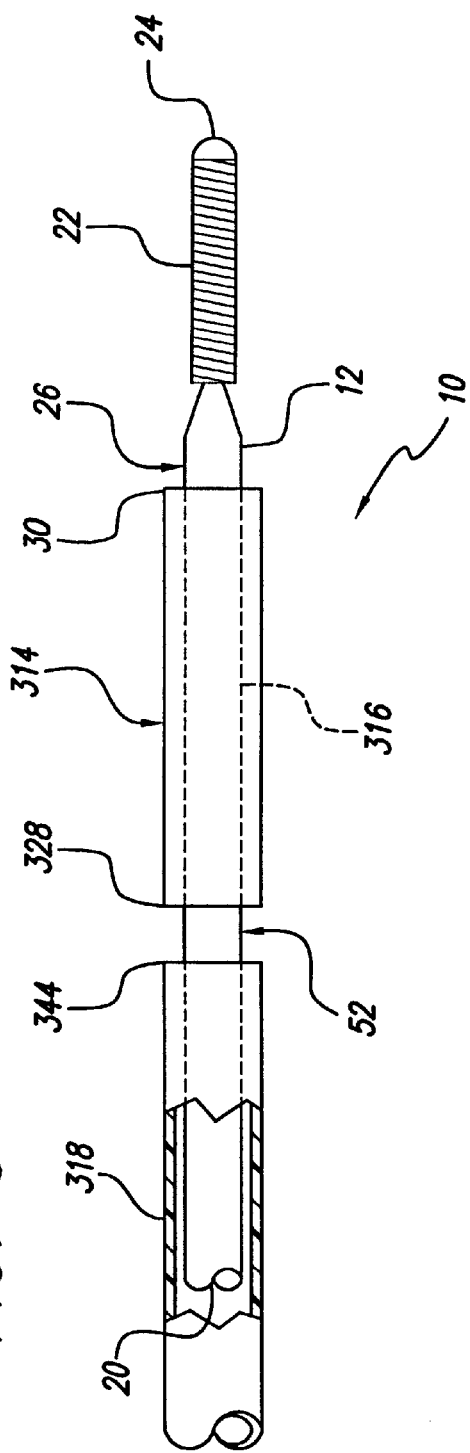
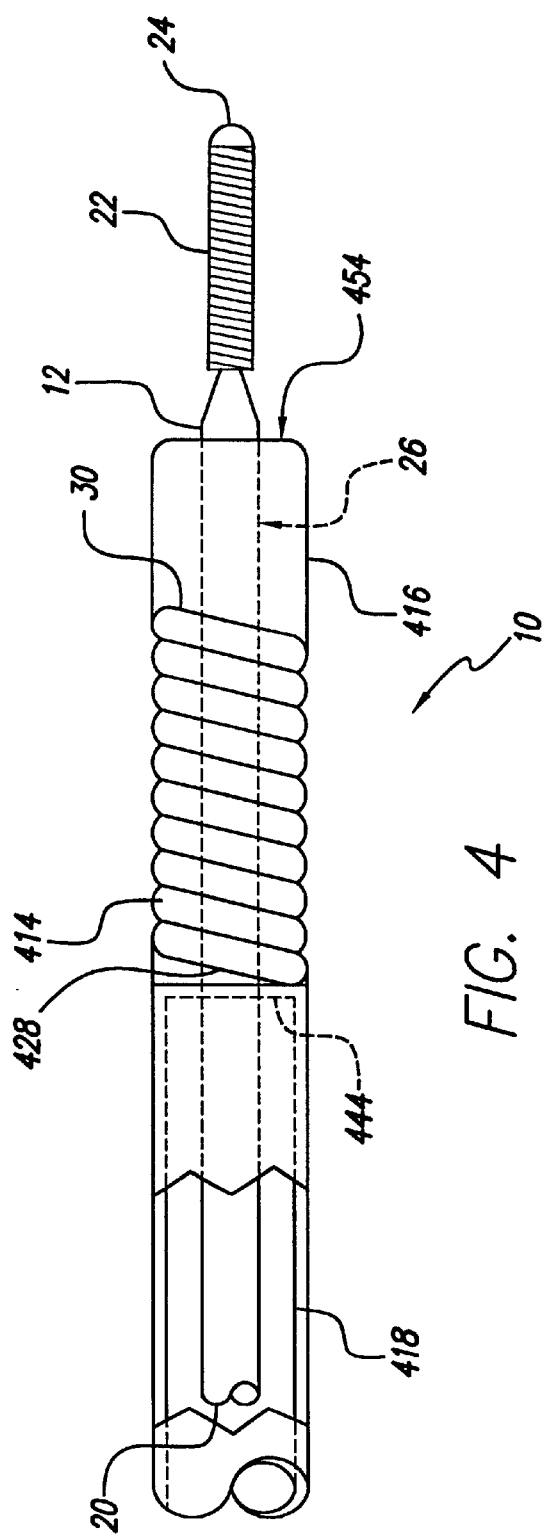

APPARATUS AND METHOD FOR DELIVERING A SELF-EXPANDING STENT ON A GUIDE WIRE

BACKGROUND OF THE INVENTION

The invention relates generally to a system and method for delivering a stent. More particularly, the invention relates to a stent delivery system (SDS) and method for delivering a self-expanding stent directly from a guide wire into a body lumen.

In typical percutaneous transluminal coronary angioplasty (PTCA) procedures, a guiding catheter having a preformed distal tip is percutaneously introduced into the cardiovascular system of a patient through the brachial or femoral arteries and is advanced therein until the distal tip thereof is in the ostium of the desired coronary artery. A guide wire and a dilatation catheter having an inflatable balloon on the distal end thereof are introduced through the guiding catheter with the guide wire slidably disposed within an inner lumen of the dilatation catheter. The guide wire is first advanced out of the distal end of the guiding catheter and is then maneuvered into the patient's coronary vasculature containing the lesion to be dilated, and is then advanced beyond the lesion. Thereafter, the dilatation catheter is advanced over the guide wire until the dilatation balloon is located across the lesion. Once in position across the lesion, the balloon of the dilatation catheter is filled with radiopaque liquid at relatively high pressures (e.g greater than about 4 atmospheres) and is inflated to a predetermined size (preferably the same as the inner diameter of the artery at that location) to radially compress the atherosclerotic plaque of the lesion against the inside of the artery to thereby dilate the lumen of the artery. The balloon is then deflated so that the dilatation catheter can be removed and blood flow resumed through the dilated artery.

A common problem that sometimes occurs after an angioplasty procedure is the appearance of restenosis at or near the site of the original stenosis in the blood vessel which requires a secondary angioplasty procedure or a bypass surgery. Another occurrence which reduces the success of an angioplasty procedure is that frequently the stenotic plaque or intima of the blood vessel or both are dissected during the angioplasty procedure by the inflation of the balloon. Upon deflation of the balloon, a section of the dissected lining (commonly called a "flap") will collapse into the bloodstream, thereby closing or significantly reducing the blood flow through the vessel. In these instances, emergency bypass surgery is usually required to avoid a myocardial infarct distal to the blockage. Side branches, tortuous vessels, and the more distal arteries have also presented serious difficulties in the PTCA procedure because of the balloon diameter.

Conceivably, the dilatation catheter could be replaced with a perfusion type dilatation catheter such as described in U.S. Pat. No. 4,790,315 in order to hold the blood vessel open for extended periods. However, perfusion type dilatation catheters have relatively large profiles which can make advancement thereof through the blockage difficult, and therefore immediate bypass surgery may be the only means of avoiding an infarct distal to the blockage or possibly even death. Additionally, the inflated balloon of these perfusion catheters can block off a branch artery, thus creating ischemic conditions in the side branch distal to the blockage.

In response, one particular endoprosthetic device, known as a stent, has been developed to prevent restenosis and repair damaged vessel walls. Stents are generally tubular shaped intravascular devices having an expandable or self-expanding structure that is placed within a damaged artery to hold it open. They are particularly suitable for supporting and holding back a dissected arterial lining which could otherwise occlude the fluid passageway there through. The use of stents in non-invasive interventional cardiology has proven to have many advantages, including a net gain in Minimal Lumen Diameter (MLD) of the vessel and reduced restenosis rates.

Stents typically are constructed in one of two general configurations: expandable, and self-expanding. Expandable stents require a mechanical force, such as exerted by a balloon disposed within the stent interior, to increase in diameter. Self-expanding stents are generally constructed of shape memory materials that are biased so that the stent diameter will increase from a reduced diameter maintained by constraining forces to an expanded diameter once the constraining forces are removed, without the action of any external mechanical forces.

Self-expanding stents may be formed in a variety of configurations, and such stents made of coiled wire or springs, braided wire or mesh, and fence-like structures configured in a zig-zag pattern are known in the art. Examples of such of these stents can be found in U.S. Pat. No. 4,655,771 (Wallsten); U.S. Pat. No. 5,405,380 (Gianotti et al.); U.S. Pat. No. 5,709,703 (Lukic et al.); and U.S. Pat. No. 5,735,871 (Sgro).

Delivery systems for self-expanding stents are generally comprised of a stent circumferentially surrounding the distal end of a delivery catheter. Due to the narrow passageways within the vascular system and particularly the stenotic regions, stents are generally confined in a reduced radius for delivery to the deployment site. Therefore, it is highly desirable to keep the profile of the catheter as small as possible to minimize the radius of the stent mounted thereon. For delivery purposes, these stents are typically held in a minimal diameter state by some structure such as a sheath. Upon displacement of the sheath, the stent is exposed to self-expand and contact the vessel wall. Once the stent is deployed, the catheter is removed, leaving the stent implanted at the desired location to keep the vessel walls from closing and allowing time to heal. Examples of devices of this type can be found in U.S. Pat. No. 5,690,644 (Yurek et al.) and U.S. Pat. No. 5,735,859 (Fischell et al.). Another device, as exemplified in U.S. Pat. No. 5,372, 600 (Beyar et al.), secures the stent to a catheter without the use of a sheath.

The choice of using a self-expanding stent delivery system instead of a balloon catheter is not without tradeoffs. Stent delivery systems for self-expanding stents using a delivery catheter tend to have larger profiles, be less flexible, and generally feel more cumbersome than their balloon counterparts. Prior art stent delivery systems are limited by the inability to navigate tortuous and narrow passageways in a reduced amount of time. These devices often include several components that require exchange during deployment.

What has been needed and heretofore unavailable is a stent delivery system capable of securing and delivering a self-expanding stent on a guide wire provided by a device offering flexibility, a lower profile, and easy handling for rapid deployment within the tortuous passageways of an anatomical lumen. The present invention satisfies these needs as well as others.

SUMMARY OF THE INVENTION

The present invention is directed to a device and method for delivering a self-expanding stent releasably secured to a guide wire that is particularly suitable for use in coronary arteries to hold vessels open after a balloon angioplasty procedure.

The guide wire stent delivery system in accordance with the present invention includes an elongated guide wire having a distal extremity encircled by a self-expanding stent which is releasably secured during delivery in a reduced cross section by a releasable retention device cooperating with a release member. The retention device may include a distal retention member and a proximal retention member. The self-expanding stent is forced into a constrained position having a low profile or reduced cross section and secured to the retention device. The stent is then introduced into a body lumen and advanced to the treatment site. Once the stent is in the desired position, an axial release force is applied to a release member to release the constrained stent from the guide wire to deploy into a high profile configuration with an enlarged cross section to support the vessel wall at the site of a stenotic lesion.

In one embodiment, a tubular mesh stent is releasably secured to a retention device comprising a hook and ring set. A distal end loop of the stent is draped over the hook portion and the proximal end of the stent is drawn back under tension to a position adjacent the ring. The distal end of the release member is threaded through the proximal end loops of the mesh stent and through the ring to secure the proximal end of the stent. The stent is then advanced through a body vessel and positioned near a treatment site. An axial displacement of the release member causes the proximal end and the distal end of the stent to be released, thereby allowing the stent to deploy into a higher profile configuration to contact the vessel walls and provide structural support thereto.

In another embodiment, a coil stent having a proximal eye and a distal eye is wrapped around the guide wire and releasably secured to the guide wire. The release member is threaded through the eyes of the stent until its distal end is slidingly disposed within a tubular retention member. The stent is released by an axial displacement of the release member.

The present invention also contemplates the use of a release member in the form of a tube that is slidingly disposed along the guide wire. In one embodiment, a hollow coil stent is threaded onto the guide wire and maintained in a generally linear configuration. The release member is displaced in the distal direction until the stent is pushed off the guide wire. Alternately, the stent is placed within a sleeve dimensioned to maintain the stent in a reduced delivery configuration. A release member is configured with a distal end to resist the proximal movement of the stent when the stent and the release member abut. Axial displacement of the release member drives the stent out the sleeve to deploy against the vessel wall.

The present invention also relates to a method of implanting a self-expanding stent using a guide wire stent delivery system according to the invention. A stent delivery system is provided with an elongated guide wire encircled by a self-expanding stent. A retention device and a release member are chosen to releasably secure the stent to the distal extremity of the guide wire. The stent is secured in a compressed, reduced profile configuration until deployment. The stent delivery system is inserted into a vessel and advanced to a treatment site. The release member is axially displaced to allow the stent to deploy against the vessel wall by self-expansion. The guide wire is then withdrawn from the vessel leaving the deployed stent in place.

Other features and advantages of the present invention will become more apparent from the following detailed description of the invention, when taken in conjunction with the accompanying exemplary drawings.

BRIEF DESCRIPTION OF THE DRAWINGS

FIG. 1 is an elevational view of the distal extremity of a stent delivery system according to the present invention.

FIG. 2 is an elevational view of the distal extremity of a second embodiment of a stent delivery system according to the present invention.

FIG. 3 is an elevational view, partially in cross-section, of the distal extremity of a third embodiment of a stent delivery system according to the present invention.

FIG. 4 is an elevational view of the distal extremity of a fourth embodiment of a stent delivery system according to the present invention.

DETAILED DESCRIPTION OF THE PREFERRED EMBODIMENTS

The present invention relates to a stent delivery system in which a self-expanding stent, releasably retained on a guide wire, is delivered into a human patient's body lumen, such as a coronary artery, carotid artery, renal artery, or peripheral artery or vein. The invention provides a guide wire stent delivery system and method of use in which a stent is implanted in a patient.

For purposes of illustration, FIG. 1 depicts stent delivery system 10 that is provided to deliver and implant self-expanding stent 14 at a treatment site within an anatomical lumen. Generally, stent delivery system 10 includes elongated guide wire 12 encircled by self-expanding stent 14 that is relcasably secured by retention device 16 and release member 18. Release member 18 actuates the release of stent 14 from retention device 16 so that the self-expanding stent deploys against the vessel wall to provide clearance for subsequent withdrawal of the guide wire and to support the vessel wall thereafter.

Still referring to FIG. 1, guide wire 12 comprises core member 20 and helical coil 22 or other flexible body disposed about and fixed to the tapered distal portion of the core member. Rounded radiopaque plug 24 is secured to the distal end of the coil, or alternatively the coil itself may be at least partially made of a highly radiopaque material such as platinum, tungsten, rhenium, ruthenium or alloys of such metals to facilitate the fluoroscopic observation of the coil when the guide wire is disposed within the patient. The rounded plug assists further in limiting any trauma to the vessel wall as the guide wire is navigated through the vasculature. Alternatively, the core member may terminate in a shaping ribbon (not shown) and plug configuration.

Elongated guide wire 12 generally has the length and configuration of a typical coronary angioplasty guide wire having both a proximal extremity (not shown) and distal extremity 26. The proximal extremity is sufficiently stiff to assist navigation and at least a portion thereof resides outside the patient to be manipulated by the physician. The distal extremity is generally more flexible than the proximal extremity to eliminate injuries to the vessel caused by the wire when it is advanced through the tortuous passageways of the vasculature.

The diameter of guide wire 12 is typical of an ordinary angioplasty guide wire, ranging from about 10 to about 35 mils and allows stent 14 to assume a smaller profile than when mounted on other delivery devices known in the art, such as a balloon catheter. Guide wire lengths from 175 cm to 300 cm are typically sufficient to access remote pathways within the patient's vasculature and extend outside the patient's system to facilitate its manipulation by the physician. Materials such as stainless steels or nickel-titanium alloys may be used to manufacture the guide wire. Other biocompatible materials may also be used. Additionally, the guide wire in the present invention may be coated with materials such as Teflon or nylon to reduce friction.

Encircling distal extremity 26 of the guide wire is self-expanding tubular stent 14. The embodiment of FIG. 1 is a mesh stent having proximal end 28 and distal end 30 encircling the distal extremity of guide wire 12 and held in a delivery configuration of reduced radius and increased axial length. This reduced radius or constrained low profile configuration may be achieved by restraining one end of the stent and axially displacing the other end of the stent away from the restrained end. The stent profile can be reduced until its inner surface is abutting the guide wire or is precluded from further compression by its own inherent characteristics. This provides an improved lower profile over those devices requiring a delivery catheter which are typically much larger than a guide wire. When stent 14 is released, it radially self expands to return to its normal state with an increased radius or distended higher profile and reduced axial length. As an alternative to stents having a mesh pattern, any pattern having cell structures known in the art would be suitable (e.g., the ACS MULTI-LINK Stent and ACS DUET Stent, marketed by Advanced Cardiovascular Systems, Inc.; the 5670 Stent and GFX Stent marketed by Medtronic AVE; and the NIR family of stents marketed by Boston Scientific Corporation).

The stent of the embodiment of FIG. 1 has an open mesh or weave construction, formed of helically wound and braided strands 32 or filaments of a resilient, preferably biocompatible material. The stent includes proximal end loops 34 and distal end loops 36 that can be used to secure the stent to the retention device.

Guide wire 12 also provides a surface for mounting releasable retention device 16. As depicted in FIG. 1, releasable retention device, generally referred to as 16, includes proximal retention member 16a and distal retention member 16b. Proximal retention member 16a consists of at least one semicircular ring secured to guide wire 12 extending out from the guide wire and formed with a hole to assist in anchoring the proximal end 28 of the stent to the guide wire. Distal retention member 16b includes at least one hook like structure secured to the guide wire at a point between coil 22 of the guide wire and the proximal retention member. The distal retention member generally projects distally and radially outwardly from the guide wire at a predetermined distance selected by the designer. The hook projects through and beyond the distal end loop 36 of the stent to releasably retain the distal end 36 of the mesh stent that is draped over the hook. The hooks 16b are preferably rounded off at the tip to prevent damage to the intima or interior surface of the vessel. Alternatively, any protruding structure that is capable of retaining one end of a mesh or similarly braided stent can be used.

Retention device 16 may be secured to the guide wire by a variety of methods. For example, the hooks and rings may be bonded, welded, or clamped onto the guide wire. Alternatively, the hooks or rings may be formed by plastic extrusion methods and slipped or threaded over the guide wire for a friction fit or secured by adhesives. Yet another alternative would entail pinching the guide wire to form a projection which could then be pierced to create a ring structure for the proximal retention member.

FIG. 1 further depicts the use of an optional protective device, comprised of a plurality of shields 38 disposed between distal retention member 16b and coil 22 of guide wire 12. Shields 38 are aligned with hooks 16b and project radially outward from the surface of the guide wire to an extent at least equal to the radially outward projection of the hooks. The shields are formed with a tapered distal end and rounded edges that cooperate with the distal end of the guide wire to provide for a smoother introduction of the distal end of the assembly into the vasculature, and thus reduced risk of injury to the vessel walls. Shields 38 may be secured to the guide wire in manner similar to the retention device.

With continued reference to FIG. 1, retention device 16 cooperates with release member 18 to releasably retain stent 14 on guide wire 12 in the reduced delivery profile during insertion and delivery of the assembly though the vasculature. Release member 18 is formed with an elongated structure that extends substantially along the length of the guide wire so that the proximal end (not shown) extends out of the patient to be manipulated by the attending physician. Release member 18 is sufficiently flexible to traverse the tortuous vasculature of the patient along with the guide wire. When the release member is used to effect proximally-directed axial motion by transmitting a tensile force applied by the physician at its proximal end, the release member may be formed with a very flexible structure that need only be strong enough to transmit such tensile forces. Release member 18 may be formed of materials such as stainless steel, NiTi alloys, or Kevlar thread, and would preferably be dimensioned to be smaller than the guide wire, preferably around six to ten mils in diameter.

Release member guide 40 is further provided to define a lumen or a track housing the release member, and thus prevent the release member from injuring the intima or getting tangled with stent 14. Referring to FIGS. 1 and 2, release member guide 40 is preferably constructed of a polymeric or metallic tubular structure defining interior lumen 42 for the purpose of housing at least a portion of release member 18. The inner diameter of the release member guide is dimensioned to reduce its profile or cross section and allow the release member to be slidably disposed therein. This tubular structure may be secured to the exterior surface of the guide wire 12 by bonding, welding, or use of adhesives.

To releasably secure stent 14 to guide wire 12, distal end loop 36 of the mesh stent is first looped over distal retention member 16b. Proximal edge 28 of the stent is next drawn back under a tensile force to reduce the profile of the stent, preferably taking advantage of the low profile of the guide wire and thus reducing the profile to the greatest extent. To secure proximal edge 28 of the mesh stent, the distal end of release member 18, which in the embodiment of FIG. 1 is in the form of a wire, is either threaded through proximal end loop 34 of the stent or around the stent and through proximal retention member 16a which is depicted in the form of a ring. Distal end 44 of the release member may be threaded through ring 16a multiple times, if necessary, to hold the stent in place, or may alternatively be formed with sufficient stiffniess to counteract the outwardly radial, self-expansion force exerted by the stent. To release the stent, the release member is drawn proximally until distal end 44 of the release member is decoupled from the proximal edge 28 of the stent, at which time the stent is able to self expand to a larger diameter where it contacts the vessel wall to provide structural support thereto. Slight axial movement of the guide wire may also be effectuated to aid the decoupling of stent distal end 30 from hooks 16b.

Alternate embodiments of the present invention are also contemplated. FIG. 2, for instance, depicts a stent configuration formed of a coil or spring. Coil stent 214 is secured to guide wire 12 by retention device 216 that cooperates with release member 218 to releasably secure the coil stent. The coil stent is configured with proximal eye 246 and distal eye 248, both dimensioned to allow release member 218 to pass therethrough. Distal end 244 of release member 218 is then inserted into distal retention member 216 which is in the form of a tubular segment for slidably receiving the distal end of the release member therein. The distal end of the release member is in the form of a wire constructed with moderate stiffness sufficient to resist the self-expansion force exerted by the stent. The distal edge of the retention device is preferably formed with a tapered edge forming protective slope 250 to provide a smooth passage of the assembly through the vasculature. The release of the stent is easily accomplished by the surgeon exerting a tensile force in the proximal direction to withdraw release member 218 from distal retention member 216 and the eyes 246 and 248 of the coil stent thereby allowing the coils of the stent to unwind and self-expansion to occur.

Another embodiment of the invention is depicted in FIG. 3. The hollow coil stent 314 may be formed from a hollow tube wound into a coil and defining an inner lumen. By unwinding, the stent can be forced into a substantially straightened state with an elongated axial length. Hollow coil stent 314 is configured with an inner diameter dimensioned to slidably receive guide wire 12 therethrough. The stent is thus stretched out into a substantially linear configuration displaying proximal end 328 and slidably disposed over distal extremity 52 of the guide wire to be frictionally retained thereon. The guide wire of the embodiment requires the flexible portion of the guide wire to be of sufficient stiffness to retain a coil stent in a straightened configuration. The stent is maintained in a substantially straightened state until deployment, which is effectuated by displacing the release member 318 in a distal direction and thus urging the stent off guide wire distal extremity 52.

The release member 318 is formed of a tubular structure of a preferably polymeric material such as polyethylene, nylon, or any other polymer known in the art. Additional stiffness may be required to apply an axial force in the distal direction to the stent or stent releasable retention device 316. The release member is dimensioned to closely conform to the outer diameter of the guide wire and remain capable of sliding along the guide wire. The release member is further configured on its distal end 344 to prevent the stent from moving in the proximal direction when the proximal edge of the stent abuts the distal portion of the release member. By sliding release member 318 in a distal direction and maintaining the guide wire in position, the stent is urged off the guide wire and thus allowed to assume its coiled configuration. Alternatively, the guide wire could be moved in the proximal direction and the release member 318 held stationary to effectuate release of the stent.

FIG. 4 depicts yet another embodiment of the present invention. Coil stent 414 is radially compressed to a reduced diameter and placed inside retention device 416 which is in the form of a tubular sleeve having a distal open end 454 and dimensioned to hold the stent therein in the reduced profile. Both the stent and the sleeve are disposed over guide wire 12. Release member 418 is in the form of a tube that is slidably disposed over the guide wire and is configured on its distal end 444 to inhibit the proximal movement of the stent when they abut. To release the stent, the retention device may be withdrawn proximally as the release member abuts the stent and holds it in place. Alternatively, the release member, while abutting the proximal edge of the stent, may be forced distally with the retention device held in place relative to the guide wire. Once the stent completely clears the distal edge of the retention device, the stent will self expand against the vessel wall. The sleeve may be manufactured from similar materials as the tubular form of the release member.

The stents as described herein may be formed from any number of materials displaying shape memory characteristics, including metals, metal alloys and polymeric materials that can be constrained in a reduced delivery profile and upon release assume an enlarged deployed diameter. Preferably, the stents are formed from metal alloys such as stainless steel, tantalum, or nickel-titanium (NiTi).

In operation, a guide wire of sufficient length, diameter, and flexibility is selected to receive and deliver a self-expanding stent. Depending on the stent being used, a corresponding retention device 16 is selected and secured around the guide wire. In FIG. 1 for example, tubular mesh stent 14 is used along with hook and ring retention device 16. While the ability to mount the retention device to any guide wire is desirable, the guide wire and retention device may be made integral thus saving the time it takes to secure the retention device to the guide wire. As previously detailed, the stent is releasably secured in a low profile state around the guide wire using the retention device.

After a vessel is punctured and an insertion shunt is in place using conventional methods, a guiding catheter is inserted into the vessel. Because a delivery catheter is not required by the present invention, the guiding catheter may be of reduced profile. Guide wire 12, with releasably secured stent 14, is inserted into the guiding catheter and both are advanced by the physician to the treatment site by manipulation of the guide wire proximal end as is well known in the art. The distal end of the guide wire is advanced out of the guiding catheter and past the treatment site so that the stent is disposed in the stenotic region needing support. Release member 18 is then actuated to apply a release force to retention device 16. An axial force in the proximal direction causes the distal end of the release member to free the proximal end of the stent, which begins to self expand. The expansion of the stent also frees distal end 30 of the stent as the loops of wire slide off distal stent hooks 16b. Upon release, the biased stent assumes a high profile, deployed configuration having a greater diameter than when constrained on the guide wire. The deployed stent inner diameter is also sufficient to provide clearance of the subsequent withdrawal of the guide wire, thus leaving the stent in place within the vessel to repair the flap or other vessel damage and support the vessel wall.

In FIGS. 3 and 4, the release member is in the form tube 318/418, respectively, that prohibits axial movement in the proximal direction when distal edge 344/444 of the release member and proximal edge 328/428 of the stent abut. The release of the stent in either of these embodiments may be accomplished by pushing the tubular release member against the stent until the stent clears the distal edge of the guide wire as in FIG. 3 or the sleeve as in FIG. 4.

While the present invention has been described herein in terms of delivering an expandable stent to a desired location within a patient's blood vessel, the delivery system can be employed to deliver stents to locations within other body lumens such as urethra or Fallopian tubes so that the stents can be expanded to maintain the patency of these body lumens. It will therefore be apparent from the foregoing that while particular forms of the invention have been illustrated and described, various modifications can be made without departing from the spirit and scope of the invention. Accordingly, it is not intended that the invention be limited, except as by the appended claims.

What is claimed:

1. A stent delivery assembly, comprising:

a guide wire having a distal portion;

a stent disposed on the distal portion of the guide wire and self-expandable from a compressed configuration to an expanded configuration;

a retainer affixed to the guide wire distal portion, the retainer configured to releasably retain the stent on the guide wire in the compressed configuration; and a release member operatively connected to the retainer to release the stent therefrom so that the stent assumes the expanded configuration.

2. The assembly of claim 1, wherein:

the release member extends along the guide wire to near a proximal end thereof.

3. The assembly of claim 2, wherein:

the retainer comprises a distal member to engage a distal end of the stent and a proximal member to releasably engage a proximal end of the stent; and the release member is operatively connected to the retainer proximal end.

4. The assembly of claim 3, wherein:

the retainer distal member is formed with barbs projecting radially outward from the guide wire.

5. The assembly of claim 4, further comprising:

a shield member disposed on the guide wire distally of the retainer distal member and projecting radially outward from the guide wire for a distance equal to or greater than the barbs.

6. The assembly of claim 4, wherein:

the retainer proximal member is disposed within the stent and includes a plurality of apertures; and the release member is formed with a distal portion removably received through the apertures to releasably secure the stent distal end to the retainer proximal member.

7. The assembly of claim 2, wherein:

the stent is formed with a distal end having an aperture and a proximal end having an aperture;

the retainer comprises a distal member disposed distally of the stent and a proximal member disposed proximally of the stent; and the release member is formed with a distal portion removably received through the retainer members and the stent apertures to releasably secure the stent distal end and stent proximal end to the guide wire distal portion.

8. The assembly of claim 7, wherein:

the retainer members are comprised of tubular structures having lumens for slidably receiving the release member distal portion therethrough.

9. The assembly of claim 8, wherein:

the stent is formed with a generally helical structure; and the release member is slidably received through the stent apertures to retain the ends of the stent in circumferentially fixed relationship to one another and prevent them from rotating to allow the stent to assume the expanded configuration.

10. A stent delivery assembly, comprising:

a stent;

a guide wire having a distal portion and including a retainer affixed thereto, the retainer configured to retain the stent in direct contact with the guide wire.

11. The stent delivery system of claim 10, wherein the stent is formed from a tube with a lumen therethrough.

12. The stent delivery system of claim 10, wherein the stent is self-expandable from a generally linear compressed configuration to an expanded configuration.

13. The stent delivery system of claim 11, wherein the guide wire is slidably received through the stent tube lumen to retain the compressed stent thereon.

14. The stent delivery system of claim 10, further comprising a tubular release member slidably disposed over the guide wire with a distal end configured to engage the stent.

15. A stent delivery assembly, comprising:

a guide wire having a distal portion;

a stent disposed over the guide wire portion and self-expandable from a compressed configuration to an expanded configuration;

a tubular retainer disposed at least over the distal portion to retain the stent thereon in the compressed configuration; and a tubular release member slidably disposed over the guide wire with a distal end configured to engage the proximal end of the compressed stent.

16. The assembly of claim 11, wherein:

the release member is slidably disposed over the guide wire with a distal end configured to urge the compressed stent out of the retainer to assume the expanded configuration.

17. The assembly of claim 11, wherein:

the release member is fixedly attached to the guide wire to prevent proximal motion of the compressed stent.

* * * * *

UNITED STATES PATENT AND TRADEMARK OFFICE
CERTIFICATE OF CORRECTION

PATENT NO. : 6,280,465 B1
DATED : August 28, 2001
INVENTOR(S) : Brett W. Cryer

It is certified that error appears in the above-identified patent and that said Letters Patent is hereby corrected as shown below:

<u>Title page,</u>
U.S. PATENT DOCUMENTS, "Marin et al." entry, change "5,456,794", to read -- 5,456,694 --.

<u>Column 10,</u>
Lines 42 and 47, change "11", to read -- 15 --.

Signed and Sealed this

Twenty-eighth Day of May, 2002

Attest:

Attesting Officer

JAMES E. ROGAN
Director of the United States Patent and Trademark Office